United States Patent
Nelson et al.

(10) Patent No.: US 10,081,594 B2
(45) Date of Patent: Sep. 25, 2018

(54) CONTROLLED CONVERSION OF DIMETHYL BENZYL ALCOHOL TO CUMENE HYDROPEROXIDE FORMED DURING THE CUMENE OXIDATION PROCESS

(71) Applicant: SABIC GLOBAL TECHNOLOGIES B.V., Bergen op Zoom (NL)

(72) Inventors: Mark Erik Nelson, Mt. Vernon, IN (US); Arkady Samuilovich Dykman, St. Petersburg (RU); Andrey Vladimirovich Zinenkov, St. Petersburg (RU); Victor Vladimiovich Pinson, St. Petersburg (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/501,185

(22) PCT Filed: Aug. 7, 2015

(86) PCT No.: PCT/IB2015/056026
§ 371 (c)(1),
(2) Date: Feb. 2, 2017

(87) PCT Pub. No.: WO2016/020897
PCT Pub. Date: Feb. 11, 2016

(65) Prior Publication Data
US 2017/0226056 A1   Aug. 10, 2017

(30) Foreign Application Priority Data

Aug. 8, 2014  (RU) .................. 2014132771

(51) Int. Cl.
| | | |
|---|---|---|
| *C08G 63/02* | (2006.01) |
| *C07C 407/00* | (2006.01) |
| *B01J 19/24* | (2006.01) |
| *C07C 45/53* | (2006.01) |
| *C07C 37/08* | (2006.01) |
| *C07C 37/20* | (2006.01) |
| *C07D 301/02* | (2006.01) |
| *C07C 1/20* | (2006.01) |
| *C08G 64/06* | (2006.01) |

(52) U.S. Cl.
CPC .......... *C07C 407/00* (2013.01); *B01J 19/245* (2013.01); *C07C 1/20* (2013.01); *C07C 37/08* (2013.01); *C07C 37/20* (2013.01); *C07C 45/53* (2013.01); *C07D 301/02* (2013.01); *C08G 64/06* (2013.01); *B01J 2219/24* (2013.01)

(58) Field of Classification Search
USPC .......................................... 528/196, 198, 212
See application file for complete search history.

(56) References Cited

U.S. PATENT DOCUMENTS

| 4,059,637 A | 11/1977 | Hosaka et al. |
| RE40,668 E | 3/2009 | Zakoshansky |

FOREIGN PATENT DOCUMENTS

| WO | 2011055206 A1 | 5/2011 |
| WO | 2011161523 A1 | 12/2011 |

OTHER PUBLICATIONS

Estrada et al., "Catalytic Activity of Iron-Substituted Polyoxotungstates in the Oxidation of Aromatic Compounds with Hydrogen Peroxide," Monatsh Chem (2010) 141: pp. 1223-1235.
International Search Report for International Application No. PCT/IB2015/056026; International Filing Date: Aug. 7, 2015; dated Dec. 11, 2015; 6 Pages.
Written Opinion of the International Searching Authority for International Application No. PCT/IB2015/056026; International Filing Date: Aug. 7, 2015; dated Dec. 11, 2015; 8 Pages.

*Primary Examiner* — Terressa Boykin
(74) *Attorney, Agent, or Firm* — Cantor Colburn LLP

(57) ABSTRACT

Systems and methods for the production of phenol and acetone from cumene oxidation products. One method includes reacting cumene and an oxidizing agent to produce a cumene oxidation product including cumene hydroperoxide and dimethyl benzyl alcohol, converting at least a portion of the dimethyl benzyl alcohol to cumene hydroperoxide by reacting the at least a portion of the dimethyl benzyl alcohol with hydrogen peroxide in both an organic phase and an aqueous to produce a converted cumene oxidation product, and cleaving the converted cumene oxidation product to produce an output product including one or more of phenol, acetone, and alpha-methylstyrene.

15 Claims, 2 Drawing Sheets

CONTROLLED CONVERSION OF DIMETHYL BENZYL ALCOHOL TO CUMENE HYDROPEROXIDE FORMED DURING THE CUMENE OXIDATION PROCESS

CROSS REFERENCE TO RELATED APPLICATIONS

This application is a 371 of International Application No. PCT/M2015/056026, filed Aug. 7, 2015, which claims priority to Russian Application No. 2014132771, filed Aug. 8, 2014 which are incorporated herein by reference in their entirety.

BACKGROUND

A well-known method for the production of phenol and acetone is oxidation of cumene with atmospheric oxygen, followed by the acid-catalytic decomposition of cumene hydroperoxide. This method permits both end products to be produced with high yield (see, for example, Kruzhalov B. D., Golovanenko B. N., Combined Production of Phenol and Acetone, Moscow, Goskhimizdat, 1964, or Kirk-Othmer Encyclopedia of Industrial Chemistry).

Methods are known for producing phenol and acetone in which, to reduce the yield of phenol tar, cumene oxidation products containing cumene hydroperoxide (CHP), cumene, and dimethylphenylcarbinol (DMPC) are cleaved in the presence of sulfuric acid. In a first stage, at a temperature of 55 to 80° C., most of the CHP (75 to 99%) is decomposed and dicumyl peroxide (DCP) is produced from DMPC and CHP. In a second stage, acetone is added at a temperature from 80 to 146° C. to the obtained reaction mixture containing phenol, acetone, dimethylphenylcarbinol (DMPC) and dicumyl peroxide (DCP). The addition is made in an amount of 1.5 to 1.8 times the original concentration of acetone. Water is also added in the process. In some cases the acid is partially neutralized with ammonia before the second separation stage in order to ensure optimal acidity of the catalyst. After breakdown of DCP formed in the first stage, decomposition of the remaining CHP and dehydration of the remaining DMPC occur at a temperature from 80 to 146° C.

These methods significantly reduce the amount of formed byproducts in comparison with decomposition in one stage (the yield of tar is 25 kg/t of phenol), whereas the amount of formed by-product (hydroxyacetone) remains at a high level (and sometimes increases). These and other shortcomings of the prior art are addressed by the present disclosure.

SUMMARY

As described herein, the disclosure, in one aspect, relates to a system comprising: (i) an oxidation reactor configured to receive a cumene feed and an oxidizing agent and to output a cumene oxidation product comprising cumene hydroperoxide and dimethyl benzyl alcohol; (ii) a conversion reactor configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and an aqueous phase (e.g., water phase) to produce a converted cumene oxidation product; (iii) a cleavage reactor configured to receive one or more of the cumene oxidation product and the converted cumene oxidation product and to produce an output product comprising one or more of phenol, acetone, and alpha-methylstyrene; and (iv) a condensation reactor configured to receive the output product and to produce one or more of Bisphenol A and para-cumylphenol.

Also disclosed are methods of reacting cumene and an oxidizing agent to produce a cumene oxidation product comprising cumene hydroperoxide and dimethyl benzyl alcohol; optionally concentrating the cumene oxidation product; causing the cumene oxidation product to pass through one or more of a first path and a second path, wherein the first path comprises a conversion reactor configured to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product, and wherein the second path circumvents the first path; and cleaving one or more of the cumene oxidation product and the converted cumene oxidation product and to produce an output product comprising one or more of phenol, acetone, and alpha-methylstyrene.

Further aspects concern systems comprising: an oxidation reactor configured to receive a cumene feed and an oxidizing agent and to output a cumene oxidation product comprising cumene hydroperoxide and dimethyl benzyl alcohol; and a conversion reactor configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product.

Additional aspects of the disclosure concern methods comprising: reacting cumene and an oxidizing agent to produce a cumene oxidation product comprising cumene hydroperoxide and dimethyl benzyl alcohol; converting at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product; and cleaving the converted cumene oxidation product to produce an output product comprising one or more of phenol, acetone, and alpha-methylstyrene.

BRIEF DESCRIPTION OF THE FIGURES

The accompanying figures, which are incorporated in and constitute a part of this specification, illustrate several aspects and together with the description serve to explain the principles of the disclosure.

Figure 1:
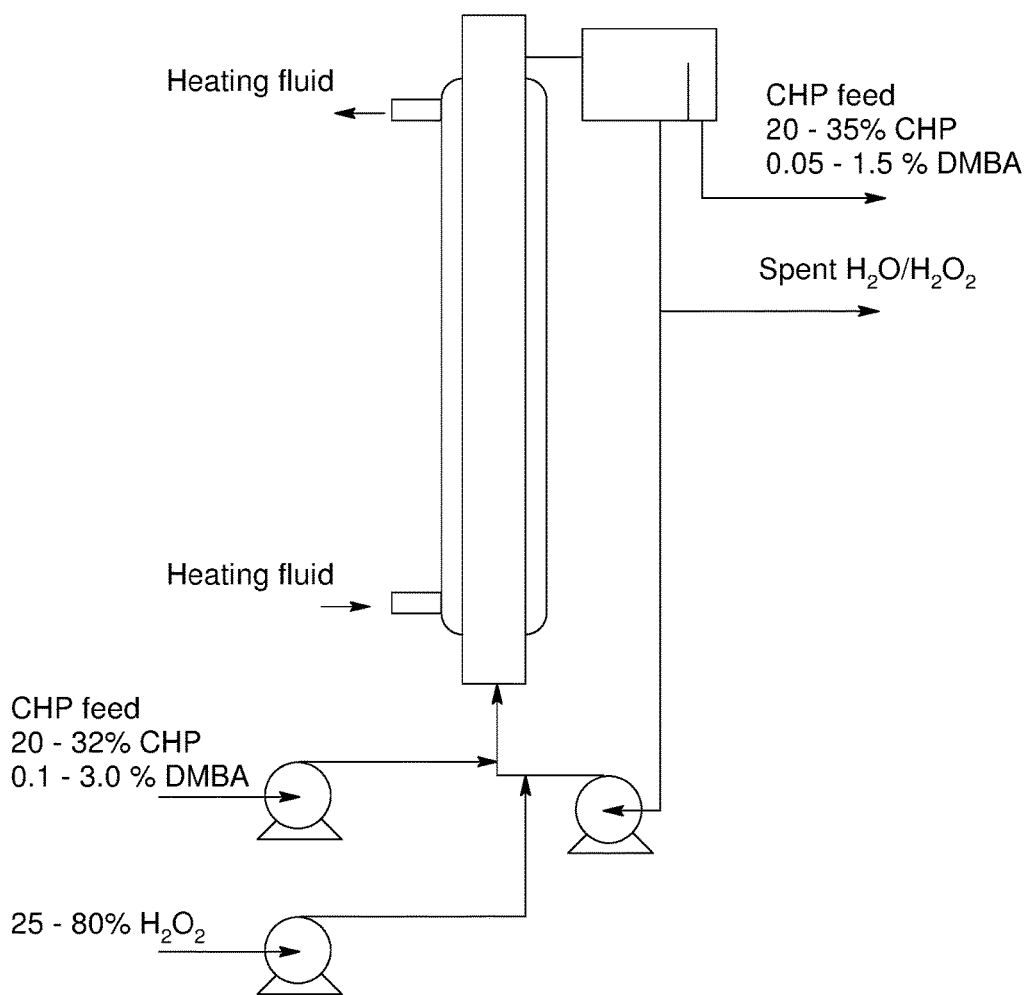
FIG. 1 shows a reactor design to carry out DMBA conversion into CHP in the aqueous phase.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DESCRIPTION

The present disclosure can be understood more readily by reference to the following detailed description of the disclosure and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed. The term "about" is intended to include any standard deviation in the measurement of the value.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Dimethyl benzyl alcohol (DMBA) is the main by-product formed in the oxidation of cumene and is responsible for the majority of the chemical by products in the phenol/acetone production process. This compound is converted to alpha-methylstyrene (AMS) in the cleavage process and is also a useful feed for the production of paracumylphenol (PCP). Ideally, the AMS production should be matched to the particular AMS requirements of the production unit, with any excess DMBA (AMS equivalents) converted to CHP to maximize the yield of phenol and acetone while minimizing heavy by-products. In one aspect of the instant disclosure, by carrying out the process in an aqueous phase one can obtain a high conversion of DMBA to CHP (greater than (>) 90% DMBA conversion in some embodiments).

In addition, by utilizing a process where the amount of the cumene oxidation product passes through one or more of a first path and a second path, the amount of DMBA conversion to CHP product can be controlled. In some embodiments, the first path comprises a conversion reactor configured to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product, and wherein the second path circumvents the first path (i.e., optionally, at least a portion the cumene oxidation product may pass directly from the oxidation reactor to the cleavage reactor).

System

In one aspect, the disclosure concerns systems comprising: (i) an oxidation reactor configured to receive a cumene feed and an oxidizing agent and to output a cumene oxidation product comprising cumene hydroperoxide and dimethyl benzyl alcohol; (ii) a conversion reactor configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product; (iii) a cleavage reactor configured to receive one or more of the cumene oxidation product and the converted cumene oxidation product and to produce an output product comprising one or more of phenol, acetone, and alpha-methylstyrene; and (iv) a condensation reactor configured to receive the output product and to produce one or more of Bisphenol A and para-cumylphenol.

In another aspect, the disclosure concerns systems comprising: an oxidation reactor configured to receive a cumene feed and an oxidizing agent and to output a cumene oxidation product comprising cumene hydroperoxide and dimethyl benzyl alcohol; and a conversion reactor configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product.

Figure 2:
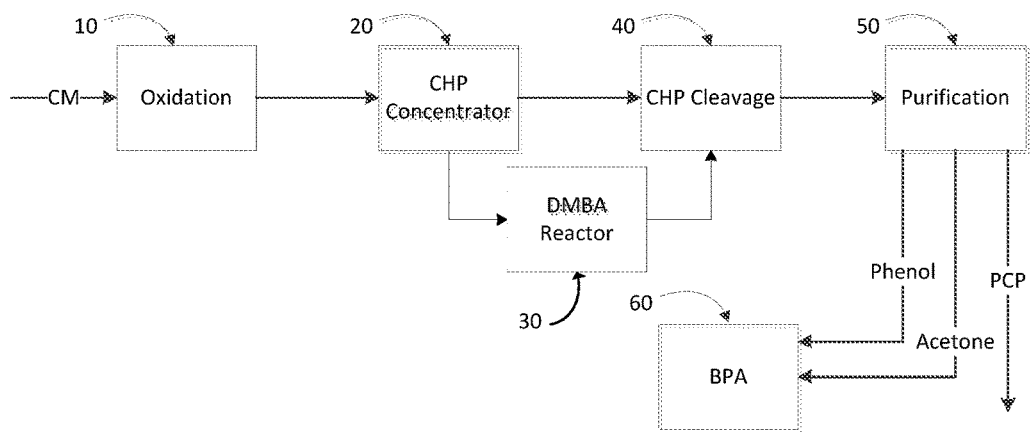
FIG. 2 shows a schematic of a system for converting cumene to phenol and acetone and ultimately to bisphenol A.

An example schematic for accomplishing certain aspects of the disclosure is found in FIG. 2. Cumene is fed to an oxidation reactor 10 to produce a cumene oxidation product comprising cumene hydroperoxide (CHP) and dimethyl benzyl alcohol (DMBA). The cumene oxidation product is fed to a CHP concentrator 20 to increase the concentration of CHP. The product of the concentrator may be fed to either a DMBA reactor 30 to convert at least a portion of DMBA to CHP or the product of the concentrator may bypass the DMBA reactor and be fed to the CHP cleavage reactor 40 where CHP is converted to a mixture comprising one or more of phenol, acetone and alpha-methylstyrene (which may be converted to paracumylphenol (PCP)). Depending on the amount of PCP desired in the process, the ratio of product from the CHP concentrator that is fed to and bypasses the DMBA reactor may be varied. The product of the CHP cleavage rector may be purified (purifier 50) to isolate acetone and phenol. The acetone and phenol can then be fed to a BPA reactor 60 to produce BPA product.

Directing the cumene oxidation product to pass through one or more of a first path and a second path may be based upon a pre-defined instruction set. Variation of the amount of reactants sent via the first and second pathways may be determined based on the amounts of the various products desired in the output product that is fed to the cleavage reactor. Instructions regarding amounts and rates of reactants passing through one or more of the first path and second path may be in a computer readable medium. The computer readable media may comprise executable instructions that when executed by a processor, directs the cumene oxidation product between the first and second paths. The computer readable media may comprise a computer or server and may be controlled primarily by computer readable instructions, which may be in the form of software or other means. Such computer readable instructions may be executed within central processing unit to cause computing system to do work. In many known workstations, servers, and personal computers, the central processing unit is implemented by a single-chip CPU called a microprocessor. In other machines, the central processing unit may comprise multiple processors.

i) Oxidation Reactor

In the first step of the cumene-to-phenol process, the cumene feed can enter an oxidation reactor (e.g., oxidation reactor 10). In one aspect, the oxidation reactor is configured to receive a cumene feed and an oxidizing agent. In another aspect, the oxidation reactor outputs a cumene oxidation product comprising cumene hydroperoxide and dimethyl benzyl alcohol.

The oxidation reactor can circulate the cumene flow through a cascade of large bubble columns. In the bubble columns, air is added at the bottom of each reactor and the oxygen can transfer from the air bubbles into the cumene. The oxidation reaction can be auto-catalyzed by the cumene hydroperoxide. The oxidation reactor can operate at pressures ranging from atmospheric to around 200 kiloPascals (kPa). The temperature of the oxidation reactor can range from 80° C.-130° C. The residence time in the reactor can range from 30 minutes to several hours.

The cumene feed can be produced, for example, from benzene and propylene. In one aspect, the cumene is produced commercially using a heterogeneous zeolite catalyst or an acid catalyst, for example, phosphoric acid and aluminum chloride.

The oxidizing agent can be any agent capable of oxidizing the cumene. In one aspect, the oxidizing agent is oxygen. The oxygen can be pure or as a mixture with other gases, for example the mixture of gases found in air. In another aspect, the oxidizing agent is air.

The cumene oxidation product comprises cumene hydroperoxide and dimethyl benzyl alcohol. The oxidation reactor can also output one or more by-products. The one or more by-products can include acetophenone (ACP) or methyl hydroperoxide (MHP) or a combination thereof.

In one aspect, the cumene oxidation product comprises from about 20 wt % to about 30 wt % cumene hydroperoxide and from about 0.1 wt % to about 3 wt % dimethyl benzyl alcohol.

ii) Stripping Element

The system may further comprise a stripping element (or CHP concentrator 20) in communication with the oxidation reactor, the stripping element configured to receive the cumene oxidation product and to modify a concentration of the cumene oxidation product, wherein the conversion reactor is configured to receive the modified cumene oxidation product. Concentrators are known to those skilled in the art. Typically the concentration of CHP would be increased in this element.

iii) Conversion Reactor

The conversion reactor (or DMBA reactor 30) may be configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product.

In an aspect, a water/$H_2O_2$ circulation to feed ratio can be greater than about 10 (e.g., 15 to 30). In another aspect, the DMBA reactor 30 has an aqueous phase to organic phase ratio of greater than about 10. As an example, a column can be used to remove the reaction water to keep hydrogen peroxide concentration at about 50%.

The converted cumene oxidation product comprises from about 20 wt % to about 32 wt % cumene hydroperoxide and from about 0.05 wt % to about 1.5 wt % dimethyl benzyl alcohol. In an example, input/output of the DMBA reactor 30 are expressed in the following table:

oxidation product, and the output product present in the cleavage reactor at a given moment. Generally this can vary from about 70° to 90° C.

The acid catalyst in the cleavage reactor can be any acidic material. To avoid corrosion, heavily corrosive inorganic acids, for example, hydrochloric acid or hydrobromic acid are not usually used in the cleavage reactor. Acid catalysts that can be used, include, for example, phosphoric acid or sulfuric acid or a combination thereof.

In one aspect, the acid catalyst can be present in the quantity of about 100 to 350 parts per million of sulfuric acid per weight of composition mass.

In some embodiments, the cleavage reaction may be run in the presence of excess acetone. In this regard, the addition of recycle acetone may be used in the stream entering the cleavage reactor (see, U.S. RE40668).

These reactors have a specific surface of about 30 to 35 meter squared per ton of 100% CHP per hour of CHP conversion in the reactors in one pass is 30 to 35%, 30 to 40%, 30 to 15%, respectively. For configurations having more or less than 3 reactors these values will be appropriately different.

Other by-products that can be formed in the cleavage reactor include, for example, hydroxyacetone, 2-methylbenzofurane, or diacetone alcohol or a combination thereof. The by-products formed in the cleavage reactor can also include some aldehydes, for example, acetaldehyde.

The output product from the cleavage reactor can be cooled. In a further aspect, the output product can be neutralized in a neutralization unit to stop the acid-catalyzed reaction from the cleavage reactor. In one aspect, the output product can be neutralized using a neutralizing agent, such as sodium phenate.

|  | MW | 1 Mass | Wt. % | 2 Mass | Wt. % | 3 Mass | Wt. % | 4 Mass | Wt. % |
|---|---|---|---|---|---|---|---|---|---|
| Cumene | 120.19 | 610.2 | 61.02 | | | 607.1 | 60.25 | 3.1 | 16.92 |
| CHP | 152.19 | 354.1 | 35.41 | | | 383.6 | 38.07 | | |
| Phenol | 94.11 | 0.2 | 0.02 | | | 7.6 | 0.76 | 0.1 | 0.55 |
| Acetone | 58.08 | 0.0 | 0 | | | 0.9 | 0.09 | 0.2 | 1.11 |
| DMBA | 136.19 | 28.4 | 2.84 | | | 2.0 | 0.20 | | |
| AMS | 118.18 | 0.2 | 0.02 | | | 0.6 | 0.06 | | |
| $H_2O$ | 18.02 | 2.2 | 0.22 | 9.5 | 49.1 | 2.3 | 0.23 | 14.7 | 81.41 |
| $H_2O_2$ | 34.01 | 0.0 | 0 | 9.9 | 50.9 | 3.4 | 0.34 | | |
| AP | 120.15 | 4.7 | 0.47 | | | 4.6 | 0.46 | | |
| Total | | 1000 | 100 | 19.4 | 100 | 1007.6 | 100.00 | 18.0 | 100.00 | iv) Cleavage Reactor

The cleavage reaction in the manufacture of phenol and acetone from cumene is well known. In the system, a feed stream from the conversion reactor (CHP cleavage reactor 40) of the cumen oxidation product and the converted oxidation product passes into the cleavage reactor. An acid catalyst in the cleavage reactor decomposes the cumen oxidation product and the converted oxidation product into an output product comprising phenol, acetone, and alpha-methylstyrene, and other by-products.

The cleavage reaction can be extremely fast due to it exothermic nature and is essentially to completion in most processes. In one aspect, the cleavage reaction can occur within 30 seconds to 5 minutes. In fact it is common to use a constant boiling or refluxing type system for the isothermal cleavage reaction. This is generally the constant boiling temperature of the cumen oxidation product, the converted V) Purification System The system may further comprise a purification system 50 that is configured to receive the output product and to purify the one or more of phenol, acetone, and alpha-methylstyrene to produce a purified output product, wherein the condensation system is configured to receive the purified output product and to produce one or more of Bisphenol A and para-cumylphenol. In some embodiments, the purification system comprises one or more distillation columns.

v) Condensation Reactor

A condensation reactor (or BPA production reactor 60) may be configured to receive the output product and to produce one or more of Bisphenol A and para-cumylphenol. Para-cumylphenol may be produced by the reaction of phenol and alpha-methylatyrene. Bisphenol A can be produced by the reaction of acetone and phenol. Methods for the production of Bisphenol A and para-cumylphenol are known in the art.

Method

The disclosure concerns methods comprising: reacting cumene and an oxidizing agent to produce a cumene oxidation product comprising cumene hydroperoxide and dimethyl benzyl alcohol; causing the cumene oxidation product to pass through one or more of a first path and a second path, wherein the first path comprises a conversion reactor configured to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product, and wherein the second path circumvents the first path; and cleaving one or more of the cumene oxidation product and the converted cumene oxidation product and to produce an output product comprising one or more of phenol, acetone, and alpha-methylstyrene.

Another method of the disclosure comprises reacting cumene and an oxidizing agent to produce a cumene oxidation product comprising cumene hydroperoxide and dimethyl benzyl alcohol; converting at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product; and cleaving the converted cumene oxidation product to produce an output product comprising one or more of phenol, acetone, and alpha-methylstyrene.

EXAMPLES

Detailed embodiments of the present disclosure are disclosed herein; it is to be understood that the disclosed embodiments are merely exemplary of the disclosure that may be embodied in various forms. Therefore, specific structural and functional details disclosed herein are not to be interpreted as limits, but merely as a basis for teaching one skilled in the art to employ the present disclosure. The specific examples below will enable the disclosure to be better understood. However, they are given merely by way of guidance and do not imply any limitation.

Dimethyl benzyl alcohol (DMBA) conversion into cumene hydroperoxide (CHP) in the presence of hydrogen peroxide takes place in both organic phase and aqueous phase in the reactions of the instant disclosure. By carrying out the process in the aqueous phase in the instant disclosure, one can obtain up to 97% DMBA conversion into CHP, which was observed using the laboratory installation presented in FIG. 1.

As shown in FIG. 1, CHP feed enters the circulation loop, containing conversion reactor, together with circulating water/hydrogen peroxide phase, where the disperse phase (CHP) passes through the layer of hydrogen peroxide water solution. Both DMBA and CHP diffusion and DMBA to CHP conversion with hydrogen peroxide takes place inside the reactor. Reactor effluent separates into organic (light) product phase and hydrogen peroxide circulation stream (heavy). Spent hydrogen peroxide stream withdrawal from circulation stream if required for maximal conversion rate is an option. CHP and DMBA-containing feed, such as cumene oxidation product after the cumene stripping, passes through the reactor with hydrogen peroxide water solution in dispersed form using common known liquid dispersing method such as static mixer, etc. A portion of the DMBA is converted to CHP. The organic layer reactor effluent is collected at the top of the column and a portion of the organic layer reactor effluent returns back to the reactor (after aqueous phase has settled from effluent). A balanced amount of low-DMBA product is directed to further processing (e.g., fed to the cleavage reactor). This process allows control of the DMBA content fed to the cleavage reactor. The phase ratio in the reactor exceeds about 10:1 water-to-organic ratio.

As seen in Table 1, the reaction rate of DMBA conversion to CHP increases as a function of hydrogen peroxide concentration. When the $H_2O_2$ concentration reaches a concentration of about 50% in the aqueous phase, high conversion percentages are observed.

TABLE 1

Reaction rate as a function of hydrogen peroxide concentration.

| $H_2O_2$ conc (wt %) | Temperature (° C.) | DMBA feed | DMBA product | Conversion (%) |
|---|---|---|---|---|
| 25 | 80 | 2.55 | 2.45 | 4 |
| 35 | 80 | 2.54 | 1.28 | 49 |
| 51 | 80 | 2.55 | 0.33 | 87 |
| 59 | 80 | 2.75 | 0.13 | 95 |

As seen in Table 2, the reaction rate of DMBA conversion to CHP increases when hydrogen peroxide concentration in the aqueous phase increases and as temperature increases.

TABLE 2

Reaction rate as a function of temperature
Conversion % of DMBA to CHP

| $H_2O_2$ conc (wt %) | temperature (° C.) | | | |
| | 60° C. | 70° C. | 80° C. | 90° C. |
|---|---|---|---|---|
| 35 wt % | | | 49% | |
| 51 wt % | | | 87% | 92% |
| 59 wt % | | 93% | 95% | |
| 70 wt % | 96% | 97% | | |

The method can simplify the conversion process as it can be carried out in the vessel without extra agitation or mixing. The only organic phase dispersing device required for the instant process is a means to produce free rising droplets of organic phase at the bottom of the column. These droplets come to the top of the column already releasing DMBA to aqueous phase and extracting CHP product.

Aspects

The disclosed compositions and methods include at least the following aspects.

Aspect 1. A system comprising: (i) an oxidation reactor configured to receive a cumene feed and an oxidizing agent and to output a cumene oxidation product comprising cumene hydroperoxide and dimethyl benzyl alcohol; (ii) a conversion reactor configured to receive the cumene oxidation product and to convert at least a portion of the dimethyl benzyl alcohol to cumene hydroperoxide by reacting the at least a portion of the DMBA with hydrogen peroxide in both an organic phase and an aqueous phase to produce a converted cumene oxidation product, wherein the ratio of aqueous phase to organic phase is greater than 10:1; (iii) a cleavage reactor configured to receive one or more of the cumene oxidation product and the converted cumene oxidation product and to produce an output product comprising one or more of phenol, acetone, and alpha-methylstyrene; and (iv) a condensation reactor configured to receive the output product and to produce one or more of Bisphenol A and para-cumylphenol.

Aspect 2. The system of aspect 1, further comprising a stripping element in communication with the oxidation reactor, the stripping element configured to receive the cumene oxidation product and to modify a concentration of the cumene oxidation product, wherein at least one of the conversion reactor and the cleavage reactor is configured to receive the modified cumene oxidation product.

Aspect 3. The system of aspect 1 or 2, further comprising a purification system configured to receive the output product and to purify the one or more of phenol, acetone, and alpha-methylstyrene to produce a purified output product, wherein the condensation reactor is configured to receive the purified output product and to produce one or more of Bisphenol A and para-cumylphenol.

Aspect 4. The system of any one of aspects 1-3, wherein the cumene oxidation product comprises from about 20 wt % to about 32 wt % cumene hydroperoxide and from about 0.1 wt % to about 3 wt % DMBA.

Aspect 5. The system of any one of aspects 1-4, wherein the converted cumene oxidation product comprises from about 20 wt % to about 35 wt % cumene hydroperoxide and from about 0.05 wt % to about 1.5 wt % DMBA.

Aspect 6. The system of any one of aspects 1-5, wherein the conversion reactor is configured to convert up to 97% of the received DMBA to cumene hydroperoxide.

Aspects 7. A method comprising: reacting cumene and an oxidizing agent to produce a cumene oxidation product comprising cumene hydroperoxide and DMBA; optionally concentrating the cumene oxidation product; causing the cumene oxidation product to pass through one or more of a first path and a second path, wherein the first path comprises a conversion reactor configured to convert at least a portion of the DMBA to cumene hydroperoxide by reacting the at least a portion of the DMBA with hydrogen peroxide in both an organic phase and an aqueous to produce a converted cumene oxidation product, and wherein the second path circumvents the first path; and cleaving one or more of the cumene oxidation product and the converted cumene oxidation product and to produce an output product comprising one or more of phenol, acetone, and alpha-methylstyrene.

Aspect 8. The method of aspect 7, further comprising reacting the output product to produce one or more of Bisphenol A and para-cumylphenol.

Aspect 9. The method of aspect 8, further comprising forming polycarbonate from one or more of the Bisphenol A and the para-cumylphenol.

Aspect 10. The method of aspect 8, further comprising forming epoxy from the Bisphenol A.

Aspect 11. The method of any one of aspects 7-10, wherein the cumene oxidation product comprises from about 20 wt % to about 32 wt % cumene hydroperoxide and from about 0.1 wt % to about 3 wt % DMBA.

Aspect 12. The method of any one of aspects 7-11, wherein the converted cumene oxidation product comprises from about 20 wt % to about 35 wt % cumene hydroperoxide and from about 0.05 wt % to about 1.5 wt % DMBA.

Aspect 13. The method of any one of aspects 7-12, wherein the conversion reactor is configured to convert up to 97% of the received DMBA to cumene hydroperoxide.

Aspect 14. The method of any one of aspects 7-13, wherein causing the cumene oxidation product to pass through one or more of a first path and a second path is based upon an instruction set in a computer readable medium.

Aspect 15. The method of any one of aspects 7-14, wherein causing the cumene oxidation product to pass through one or more of a first path and a second path is based upon a concentration of one or more of phenol, acetone, and alpha-methylstyrene in the output product.

Aspect 16. The method of any one of aspects 7-15, wherein causing the cumene oxidation product to pass through the select one or more of the first path and the second path comprises causing a first portion of the cumene oxidation product to pass through the first path and a second portion of the cumene oxidation product to pass through the second path.

Aspect 17. The method of any one of aspects 7-10 and 14-16, comprising the concentrating of the cumene oxidation product before causing the cumene oxidation product to pass through the one or more of the first path and the second path.

Aspect 18. The method of aspects 17, wherein the cumene oxidation product comprises from about 60 wt % to about 90 wt % cumene hydroperoxide and from about 0.4 wt % to about 10 wt % DMBA, preferably comprising about 75 wt % to about 85 wt % cumene hydroperoxide.

Aspect 19. A system comprising: an oxidation reactor configured to receive a cumene feed and an oxidizing agent and to output a cumene oxidation product comprising cumene hydroperoxide and DMBA; and a conversion reactor configured to receive the cumene oxidation product and to convert at least a portion of the DMBA to cumene hydroperoxide by reacting the at least a portion of the DMBA with hydrogen peroxide in both an organic phase and an aqueous to produce a converted cumene oxidation product.

Aspect 20. The system of aspect 19, wherein the cumene oxidation product comprises from about 20 wt % to about 32 wt % cumene hydroperoxide and from about 0.1 wt % to about 3 wt % DMBA.

Aspect 21. The system of aspect 19 or 20, wherein the converted cumene oxidation product comprises from about 20 wt % to about 35 wt % cumene hydroperoxide and from about 0.05 wt % to about 1.5 wt % DMBA.

Aspect 22. The system of any one of aspects 19-21, wherein the conversion reactor is configured to convert up to 97% of the received DMBA to cumene hydroperoxide.

Aspect 23. The system of any one of aspects 19-22, further comprising a cleavage reactor configured to receive one or more of the cumene oxidation product and the converted cumene oxidation product and to produce an output product comprising one or more of phenol, acetone, and alpha-methylstyrene.

Aspect 24. A method comprising: reacting cumene and an oxidizing agent to produce a cumene oxidation product comprising cumene hydroperoxide and DMBA; converting at least a portion of the DMBA to cumene hydroperoxide by reacting the at least a portion of the DMBA with hydrogen peroxide in both an organic phase and an aqueous to produce a converted cumene oxidation product; and cleaving the converted cumene oxidation product to produce an output product comprising one or more of phenol, acetone, and alpha-methylstyrene.

Aspect 25. The method of aspect 24, further comprising condensing the output product to produce one or more of Bisphenol A or para-cumylphenol, or both.

Aspect 26. The method of aspect 24 or 25, further comprising forming polycarbonate from one or more of the Bisphenol A and the para-cumylphenol.

Aspect 27. The method of any one of aspects 24-26, further comprising forming epoxy from the Bisphenol A.

Aspect 28. The method of any one of aspects24-27, wherein the cumene oxidation product comprises from about 20 wt % to about 32 wt % cumene hydroperoxide and from about 0.1 wt % to about 3 wt % DMBA.

Aspect 29. The method of any one of aspects 24-28, wherein the converted cumene oxidation product comprises from about 20 wt % to about 35 wt % cumene hydroperoxide and from about 0.05 wt % to about 1.5 wt % DMBA.

Aspect 30. The method of any one of aspects 24-28, wherein up to about 97% of the received DMBA is converted to cumene hydroperoxide.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system comprising:
    an oxidation reactor configured to receive a cumene feed and an oxidizing agent and to output a cumene oxidation product comprising cumene hydroperoxide and dimethyl benzyl alcohol;
    a conversion reactor configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and a aqueous phase to produce a converted cumene oxidation product, wherein the ratio of aqueous phase to organic phase is greater than 10:1;
    a cleavage reactor configured to receive one or more of the cumene oxidation product and the converted cumene oxidation product and to produce an output product comprising one or more of phenol, acetone, and alpha-methylstyrene; and
    a condensation reactor configured to receive the output product and to produce one or more of Bisphenol A and para-cumylphenol.

2. The system of claim 1, further comprising a stripping element in communication with the oxidation reactor, the stripping element configured to receive the cumene oxidation product and to modify a concentration of the cumene oxidation product, wherein at least one of the conversion reactor and the cleavage reactor is configured to receive the modified cumene oxidation product.

3. The system of claim 1, further comprising a purification system configured to receive the output product and to purify the one or more of phenol, acetone, and alpha-methylstyrene to produce a purified output product, wherein the condensation reactor is configured to receive the purified output product and to produce one or more of Bisphenol A and para-cumylphenol.

4. A method comprising:
    reacting cumene and an oxidizing agent to produce a cumene oxidation product comprising cumene hydroperoxide and dimethyl benzyl alcohol;
    optionally concentrating the cumene oxidation product to increase the amount of cumene hydroperoxide in the cumene oxidation product;
    causing at least a portion of the cumene oxidation product to pass through a first path, wherein the first path comprises a conversion reactor configured to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product;
    optionally causing a portion of the cumene oxidation product to pass through a second path, wherein the second path circumvents the first path; and
    cleaving one or more of the cumene oxidation product and the converted cumene oxidation product to produce an output product comprising one or more of phenol, acetone, and alpha-methylstyrene.

5. The method of claim 4, further comprising condensing the output product to produce one or more of Bisphenol A and para-cumylphenol.

6. The method of claim 5, further comprising
    forming polycarbonate from one or more of the Bisphenol A and the para-cumylphenol; or
    forming epoxy from the Bisphenol A.

7. The method of claim 4, wherein the cumene oxidation product comprises from about 20 wt % to about 30 wt % cumene hydroperoxide and from about 0.1 wt % to about 3 wt % dimethyl benzyl alcohol.

8. The method of claim 4, wherein the converted cumene oxidation product comprises from about 20 wt % to about 35 wt % cumene hydroperoxide and from about 0.1 wt % to about 1.5 wt % dimethyl benzyl alcohol.

9. The method of claim 4, wherein the conversion reactor is configured to convert greater than about 97% of the received dimethyl benzyl alcohol to cumene hydroperoxide.

10. The method of claim 4, wherein the method comprises causing the portion of the cumene oxidation product to pass through the second path based upon an instruction set in a computer readable medium.

11. The method of claim 4, wherein the method comprises causing the portion of the cumene oxidation product to pass through the second path based upon a concentration of one or more of phenol, acetone, and alpha-methylstyrene in the output product.

12. The method of claim 4, wherein the method comprises causing the portion of the cumene oxidation product to pass through the second path.

13. The method of claim 4, wherein the ratio of aqueous phase to organic phase is greater than 10:1.

14. A system comprising:
    an oxidation reactor configured to receive a cumene feed and an oxidizing agent and to output a cumene oxidation product comprising cumene hydroperoxide and dimethyl benzyl alcohol; and
    a conversion reactor configured to receive the cumene oxidation product and to convert at least a portion of the dimethyl benzyl alcohol to cumene hydroperoxide by reacting the at least a portion of the dimethyl benzyl alcohol with hydrogen peroxide in both an organic phase and an aqueous phase to produce a converted cumene oxidation product.

15. The system of any claim 14, further comprising a cleavage reactor configured to receive one or more of the cumene oxidation product and the converted cumene oxidation product and to produce an output product comprising one or more of phenol, acetone, and alpha-methylstyrene.

* * * * *